United States Patent [19]

Edelmann et al.

[11] Patent Number: 4,676,952

[45] Date of Patent: Jun. 30, 1987

[54] PHOTOMETRIC ANALYSIS APPARATUS FOR A LIQUID

[75] Inventors: Hermann Edelmann, Tutzing-Unterzeismering; Manfred Pasch, Tutzing; Karlheinz Mann, Weilheim; Stephan Sattler, Socking; Hans-Peter Haar, Weilheim, all of Fed. Rep. of Germany

[73] Assignee: Boehringer Mannheim GmbH, Mannheim, Fed. Rep. of Germany

[21] Appl. No.: 603,521

[22] Filed: Apr. 24, 1984

[30] Foreign Application Priority Data

Apr. 25, 1983 [DE] Fed. Rep. of Germany ....... 3314961

[51] Int. Cl.⁴ ..................... G01N 21/13; G01N 35/04
[52] U.S. Cl. ....................................... 422/72; 422/64; 436/45; 436/48
[58] Field of Search ..................... 422/63, 64, 65, 67, 422/72, 102, 104; 436/45, 48, 50; 414/222, 225, 417; 494/16, 19, 20

[56] References Cited

U.S. PATENT DOCUMENTS

| | | | |
|---|---|---|---|
| 3,679,130 | 7/1972 | Mayo et al. | 494/20 |
| 4,133,642 | 1/1979 | Nosaka et al. | 422/66 |
| 4,296,069 | 10/1981 | Smith et al. | 422/65 |
| 4,296,070 | 10/1981 | Montalto et al. | 422/65 |
| 4,515,889 | 5/1985 | Klose et al. | 436/45 |

Primary Examiner—Barry S. Richman
Assistant Examiner—C. M. Delahunty
Attorney, Agent, or Firm—Felfe & Lynch

[57] ABSTRACT

A photometric liquid analysis apparatus of the centrifugal analysis type uses insert elements having an elongated body, an optical measurement chamber near one end of the elongated body and a positioning trough on one side of the elongated body. The photometric liquid analysis apparatus has a rotor for rotating the insert elements to photometric means for photometric analysis of a liquid then in the optical measurement chamber of the insert element during the rotation of the rotor. The rotor has radial guiding chambers, each having an opening at an end thereof adjacent the outer periphery of the rotor and a configuration for receiving one of the insert elements with its positioning trough on a lateral side thereof and adjacent the outer periphery of the rotor. A fixed element on the rotor is on a lateral side of each guiding chamber circumferentially spaced from the positioning trough of the insert element therein when the insert element is initially received in the guiding chamber and an adjustment device moves the received insert element circumferentially into a second position engaging the fixed element with the positioning trough thereof.

13 Claims, 13 Drawing Figures

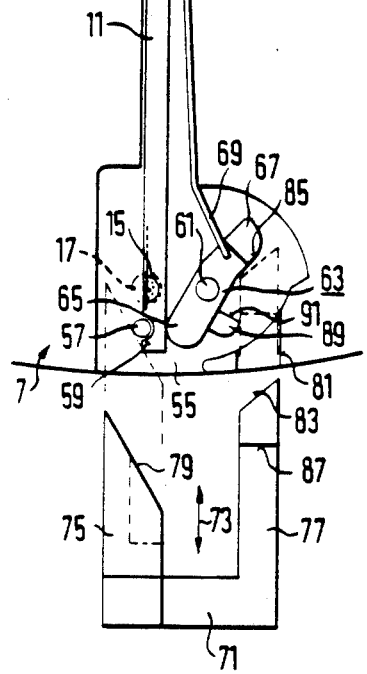
FIG. 3
FIG. 4
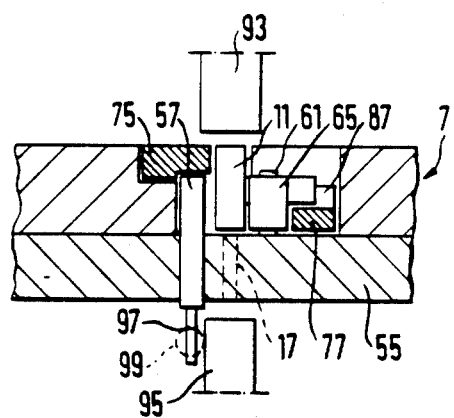
FIG. 5

PHOTOMETRIC ANALYSIS APPARATUS FOR A LIQUID

BACKGROUND OF THE INVENTION

The present invention is concerned with a liquid analysis apparatus and, more particularly, holding and positioning an analysis insert element on a rotor thereof.

A centrifugal analysis apparatus is known from Federal Republic of Germany Patent Specification No. 30 44 385. It is used for clinical chemical analysis, especially of components of blood and serum, as a basis for medical diagnosis. The liquid sample to be measured is introduced into the insert element and, by centrifuging, mixed with reagent contained in the insert element. Besides the optical measurement chamber, the insert element can contain several mixing chambers which are connected together in such a manner that the liquid can flow over between the individual chambers in the case of appropriate control of the rotor movement. Thus, by control of the rotor movement, the mixing with reagents, the incubation and the course of the reaction can be controlled. The reagents can, for example, be dry reagents introduced into the insert elements by the manufacturer. However, liquid reagents can also be used. With the help of such an analysis apparatus of the rotor type, several liquid samples can be investigated simultaneously, which considerably reduces the time needed for the analysis. In the case of the known centrifugal analysis apparatus, the rotor is constructed as a flat, circular disc upon which the insert elements can be fixed around the axis of rotation at an angle to each other.

A photometer which is especially useful for a centrifugal analyser of the above type is known from Federal Republic of Germany Patent Specification No. 29 30 431. This is a polychromic photometer which permits the measurement of the parameters of a plurality of samples on a rotor in a particularly short time and at several selectable light wavelengths.

From U.S. Patent Specification No. 3,713,775, there is known a centrifugal analysis apparatus in the case of which several insert elements provided with the sample liquid to be measured are assembled together by means of a flexible carrying body to give a unit. The carrying body, bent round the axis of rotation of the rotor, is fixed on to the rotor, the insert elements running radially to the axis of rotation of the rotor. The carrying body fixes and positions the insert elements relative to the beam path of the photometer. The carrying element is placed from above radially on the rotor.

Another centrifugal analysis apparatus is known from U.S. Patent Specification No. 4,135,883. In the case of this analysis apparatus, the rotor has, axially to its axis of rotation, pockets which are accessible from above, into which pockets the insert elements can be inserted and clamped.

In the case of the known analysis apparatus, only relatively few insert elements can be simultaneously fixed to the rotor. The transillumination surface of the measurement chamber is comparatively large in order to provide substantially constant measurement conditions of the photometer, even in the case of low requirements for positioning exactitude. Furthermore, in the case of the known analysis apparatus, the insert elements are placed radially from above on to the rotor. During operation, the insert elements are freely subjected to the ventilator action of the rotor and are uncontrollably cooled by the air flow produced. Insofar as the rotor rotates in a fixed-positioned housing and is to be maintained by means of a heating device at a predetermined temperature level, only relatively wide temperature limits can be maintained since, for the insertion of the insert elements, a large housing opening is necessary.

It is an object of the present invention to provide an analysis apparatus for the photometric determination of a parameter of a liquid, especially a centrifugal analysis apparatus, in the case of which the opening section of the rotor necessary for the insertion of the insert elements is as small as possible in order to simplify the maintaining constant of the rotor temperature. Furthermore, the holding of the insert elements is to be constructed in such a manner that an automatic insertion of the insert elements is also to be possible with only a small constructional expense. In addition, the rotor is to be capable of simultaneously accommodating and exactly positioning a large number of insert elements.

According to the present invention, this object is achieved in that the holding means are constructed as guiding chambers which are radial to the axis of rotation of the rotor and outwardly open peripherally. The insert elements, each having an elongated body with the optical measurement chamber near one end of the elongated body and a positioning trough on one side of the elongated body, can be respectively inserted into the guiding chambers substantially radially to the axis of rotation of the rotor with the positioning trough of each insert element on a lateral side thereof and adjacent the outer periphery of the rotor. Positioning and holding means on the rotor position the optical measurement chamber of each insert element in its respective guiding chamber at a position adjacent the outer periphery of the rotor and hold the insert element therein during the rotation of the rotor. For this, the positioning and holding means has a fixed element in a fixed position relative to the rotor on a lateral side of each guiding chamber at a position adjacent the outer periphery of the rotor and facing the positioning trough of the insert element circumferentially spaced therefrom when the insert element is initially received in its respective guiding chamber in a first position therein, and adjustment means. The adjustment means move the received insert element circumferentially into a second position engaging said fixed element with the positioning trough thereof, whereby said positioning trough and said fixed element are in a locking configuration in said second position.

The insert elements are inserted radially into the rotor from the outside through an opening with a relatively small cross-section, the rotor preferably being located in an insert element exchange position by means of a substantially radially movable locking means. The insertion can take place by a relatively simple automatic insertion device. The positioning and holding means not only locate the insert element in the guiding chamber but also align the measurement chamber exactly to the optical beam path of the photometric measurement apparatus. The exact alignment is necessary since the transillumination cross-section of the measurement chamber is very small because of its small volume. The analysis device according to the present invention fulfils relatively high tolerance requirements. In the case of a rotor diameter of 320 mm. and a speed of rotation of 3000 r.p.m., radial and tangential tolerances of the measurement chamber relative to the optical beam path of the photometric measurement apparatus of, for example, 50 μm. can be maintained.

The positioning and holding means alternatively could be a trough provided in the wall of the guiding chamber, a lug or rib formed on to the insert element engaging flatly into this trough. Since the production of such a positioning trough can involve difficulties, the preferred positioning and holding means is formed as a pin projecting parallel to the axis of rotation of a rotor and the positioning trough is on the insert element.

The pin preferably passes completely through the base disc of the rotor and emerges again on the side of the base disc axially remote from the holding means. The emerging end of the one-piece pin forms a guide pin for a control light barrier of the photometer. In this way, the measurement tolerances between the guide pin and the measurement chamber of the positioned insert element are further reduced.

The guiding chambers are preferably almost completely closed by walls on the rotor and/or by walls on the frame of the apparatus arranged at a small distance from the rotor and parallel to its outer surfaces. The convection cooling of the insert elements in the case of rotation of the rotor and the evaporation of the contents of the insert elements is, therefore, comparatively small. The guide chambers can hereby be utilised as air-conducting canals which bring tempered air from a temperature-regulating air source into close heat-exchange contact with the insert elements, which improves the time constancy of the regulation.

In a first preferred embodiment, an adjustment means is provided on the rotor as a tiltably mounted lever, which acts as a positioning element, and is pre-stressed by a spring against the insert element in the direction towards the positioning and holding means. Instead of or also in addition to the spring, for the production of the prestressing there can also be used a fly-weight which becomes effective when the rotor is rotating. The lever presses the positioning means for the insert element against the complementary positioning and holding means, whereby the measurement chamber of the insert element, which is preferably closely adjacent to the positioning means becomes aligned relative to the rotor and its indexing means controlling the photometric measurement apparatus and is simultaneously located.

On the apparatus frame, there can be provided a movable lock as locking means which, when the rotor is stationary in a pre-determined insert element exchange position, can be moved into the tilt path of the lever. The locking means non-rotatably locks the rotor, standing in the insert element exchange position, on the apparatus frame so that this cannot rotate during the exchange of the insert elements. On the locking means, there is provided an impingement face facing counter to the insertion movement of the locking means, which co-operates with a stop face on the lever. The stop face is so constructed that, in the case of an insert element being inserted into the guiding chamber but incorrectly positioned, it prevents the pulling out of the locking means and thus the operation of the apparatus. The throwing out of non-located insert elements during the centrifugal operation is thus prevented with certainty.

The locking means preferably forms a constructional unit with an ejector which brings the positioning means of the insert element and of the positioning and holding means out of engagement when the locking means is present in the tilting path of the lever and thus moves them apart counter to the direction of prestressing of the lever in the circumferential direction of the rotor. Because of its stopping function, the locking means can only be moved back after removal of the ejected insert element from the rotor.

In a second preferred embodiment, the adjustment means has a spring engaging between the positioning element and the rotor, which spring forcefully presses the positioning element, movable in the circumferential direction of the rotor, against the rotor-fixed part of the contact face of the positioning organ of the holding means. This rotor-fixed part of the positioning and holding means can be a side wall of the guiding chamber. In this embodiment, the opening cross-section of the guiding chamber is particularly small. For the tempering of the insert element by air flowing along it, an essentially close contact can be maintained over the whole length of the insert element, which facilitates the maintenance of a desired temperature.

In the stress path between the spring and the positioning element, there is preferably provided a pressure piece slidably guided on the rotor. By means of an operational part movably guided on the apparatus frame, which part can, when the rotor is stationary, be moved into the path of movement of the pressure piece, on the one hand the rotor can be locked and, on the other hand, the pressure piece can be lifted up, counter to the force of the spring, from the positioning element. A thrust surface on the operational part moves the positioning element out of its engagement position positioning the insert element. The spring force is hereby taken up from the operational part directly and not via the positioning element, which increases the life of the positioning element.

The pressure piece is mounted substantially radially movably on the rotor and has a wedge-shaped sliding surface directed radially outwardly obliquely to the circumferential direction, which sliding surface, by the action of the force of the spring, pushes the positioning element to the insert element. For the accommodation of the spring, formed, for example as a helical pressure spring, there is a relatively large amount of space available in the radial direction towards the rotor. Consequently, the spring can be strongly dimensioned so that the insert element itself can then be surely pressed on its contact faces if, because of constructional inexactitudes, it should be bent. The pressing-on force can be further increased by an appropriate choice of the engagement angle of the wedge-shaped sliding surface.

In the case of this embodiment, too, for the reduction of the positioning tolerances, the control pin of a control light barrier is not applied to a base disc of the rotor but on the positioning element. The control pin projects through an opening of the base disc.

A further reduction of the positioning tolerances is obtained when the stop trough and the measurement chamber are closely adajacent. Finally, for the further reduction of the positioning tolerances in the case of insert elements constructed as synthetic resin formed parts, the stop trough and the greater part of the inner wall of the measurement chamber are shaped by the shaped surface of a common, one-piece shaping tool part of an injection moulding apparatus.

The analysis apparatus can, without problems, be automatically loaded with insert elements. In a constructively simple embodiment, on the apparatus frame there is movably provided at least one magazine which has a plurality of recesses for insert elements open towards the rotor. The magazine can be a drum with axis-parallel recesses distributed on the circumferential mantle or a disc with radially-running, trough-shaped recesses staggered in the circumferential direction. Especially simple magazines have a tray shape and carry the insert elements in recesses which are parallel to one another and are especially trough-shaped. A transport device co-ordinates the recesses successively to the insert path of the guiding chambers of the rotor which are stationary in a predetermined insert element exchange position and pushes the insert elements out of the magazine into the guiding chambers or from the guiding chambers into the magazine.

For this purpose, the transport device can have a slide movably mounted radially to the axis of rotation of the rotor, the slide having gripping means for gripping the insert elements. The recesses of the magazine, the guiding chambers and guiding surfaces extending along the slide guide form a substantially continuous, straight-lined guiding canal in which the insert elements lie movably. Therefore, the gripping means must not be immovably coupled with the insert elements. It suffices when it can push or draw the insert elements along the guide canal. The gripping means can be constructed as a simple carrier movably held on the slider.

In order not to have to apply an electrical drive on the slider for the movement of the gripping means, and consequently to avoid having electrical leads following the slider movement, it is preferably provided that the transport device has, on the apparatus frame, a cam rod rotatably mounted about an axis parallel to the slider guide, along which the gripping means slides in the case of movement of the slider. The cam rod is rotated by a motor fixed on the apparatus frame or the like and, in a first rotational position, brings the gripping means into engagement with the insert element and, in a second rotational position, out of engagement.

The insert elements are preferably provided with a magnetic data carrier layer on one of their surfaces which, seen laterally, are in the direction of movement. On the data carrier layer there can be stored characterising data of the liquid sample to be measured, as well as programme data concerning the specific chronological rotation programme for the insert element used. By means of a magnet head, the data can be read off upon conveying the insert element to the magazine or to the rotor and can possibly be supplemented by result data or the like.

The transducer slot of the magnet head must, over its whole length, lie against the data carrier layer of the insert element. For this purpose, the magnet head and/or a guide part for the insert element associated therewith must be movably mounted. In a preferred embodiment, the guide part has two guiding surfaces which are parallel in the direction of movement of the insert elements and, away from the magnet head, are inclined towards one another, for the edge guiding of adjacent, parallel longitudinal edges of the insert element. In this way, the insert element can tilt about its longitudinal axis and lie against the magnet head. In addition, the magnet head is preferably suspended cardanically, for example, on a leaf spring running substantially parallel to the data carrier layer.

For sufficiently exact measurement results, the reactions in the insert elements must be carried out at a constant, predetermined temperature of, for example, 37° C.±0.1° C. The maintaining constant of the temperature takes place extraordinarily well when the inner chamber of the rotor receiving the insert elements is substantially closed and can be supplied via a central opening of the rotor with air from a source of air temperature controlled by means of a first control circuit. As already mentioned, the inner chamber of the rotor can hereby be closed off by non-rotating walls or by walls fixed to the housing. In particular, the guiding chambers are so constructed that they form radial air conducting canals along the insert elements and essentially completely enclose the insert elements. The air eddying in the case of rotation of the rotor has, in this way, only a very small influence on the temperature in the region of the insert elements. The tempered air introduced via the central opening is substantially utilised for the tempering of the insert elements.

The special air introduction in the rotor region has, as a result, an especially short time constant for the temperature regulation. This can thereby be advantageously utilised in that, during the loading procedure of the insert elements, the air introduction is completely switched off, in order to reduce evaporation phenomena. It suffices again to switch on the air introduction shortly before the measurement. Furthermore, even with a single regulating circuit, this type of air introduction permits the temperature to be adjusted sufficiently constantly in the region of the rotor. However, for the further improvement of the temperature regulating properties, the rotor can additionally be arranged in a substantially closed housing forming or enclosing the apparatus frame, the inner air temperature of the housing being capable of temperature regulation via a heating device by means of a second regulating circuit. A control controlling the rotation of the rotor can, in the case of centrifugal operation, possibly change the desired temperature value of the first regulating circuit a predetermined period of time before commencement of the centrifugal operation by a predetermined temperature value. Thus, for example, it can decrease the temperature in order to counter the temperature change due to surrounding air being sucked into the housing by the rotation.

For the measurement of the actual temperature at the place of the insert elements, it is preferable to provide in one of the guiding chambers of the rotor a temperature sensing device in a housing corresponding to the shape of the insert element. The signals corresponding to the measured temperature can be transmitted via optocouplers or via sliding rings or the like to the control and possibly to the regulating circuits.

It is to be stressed that the above-explained temperature control can also be employed in the case of other forms of analysis apparatus.

A further aspect of the present invention, which can also be employed in the case of analysis apparatus other than the above explained apparatus, provides a way of reducing the imbalance of the rotor in a simple manner in the case of partial loading, especially when the total number of the insert elements to be loaded is not fixed before the loading. For this purpose, the loading operation of the rotor can be controlled by a control which, after loading of a predetermined number of adjacent guiding chambers of the rotor with insert elements in a constant rotational loading direction, alternatingly there is loaded either a predetermined number of adjacent guiding chambers lying essentially diametrically opposite to the last supplied of the guiding chambers or there is loaded a predetermined number of again adjacent guiding chambers with insert elements adjacent the last supplied holding means. The predetermined number corresponds to the number of insert elements producing the maximum permissible imbalance. Since the rotor does not have to be rotated through about 180° after each loading step but rather, in each case, alternatingly adjacent and diametrically opposite lying guiding chambers are loaded, the loading and unloading time of the rotor can be kept relatively short in spite of the balancing of the imbalance. In order to keep the imbalance as small as possible, after the loading in each case of a single guiding chamber, subsequently the approximately diametrically opposite-lying guiding chamber and the immediately adjacent guiding chamber in the rotational loading direction is, in each case, loaded with an insert element. The unloading of the rotor can take place correspondingly.

According to another aspect of the present invention, which can also be used in the case of analysis apparatus other than according to the present invention, for the avoidance of imbalance phenomena in the case of loading and unloading of the rotor, the rotor carries, for each guiding means, a flyweight movable radially between an inner and an outer position, the insert element inserted into the guiding chamber locating the flyweight of its guiding chamber in the inner position. The inner position, the outer position, as well as the weight of the flyweight and of the insert element are so coordinated with one another that the flyweight in the outer position produces essentially the same centrifugal force as the flyweight located in the inner position by the insert element and the insert element together. In the case of radially insertable insert elements, the flyweight is preferably radially displaceable on the rotor and, in the case of the insertion of the insert element, is taken along by this form the outer position into the inner position. The flyweight is preferably a component of the regulating means, for example an arm of the above-mentioned lever or the pressure piece.

The various aspects of the present invention will now be described in more detail, with reference to the accompanying drawings, in which:

FIG. 3 is a schematic partial view of a rotor of the analysis apparatus according to FIG. 1 with an inserted and positioned insert element;

FIG. 4 is a schematic partial view of the rotor according to FIG. 3 but with the insert element deflected from the positioned position;

FIG. 5 is a radial view of the rotor opening seen along the line V—V of FIG. 4;

Figure 1:
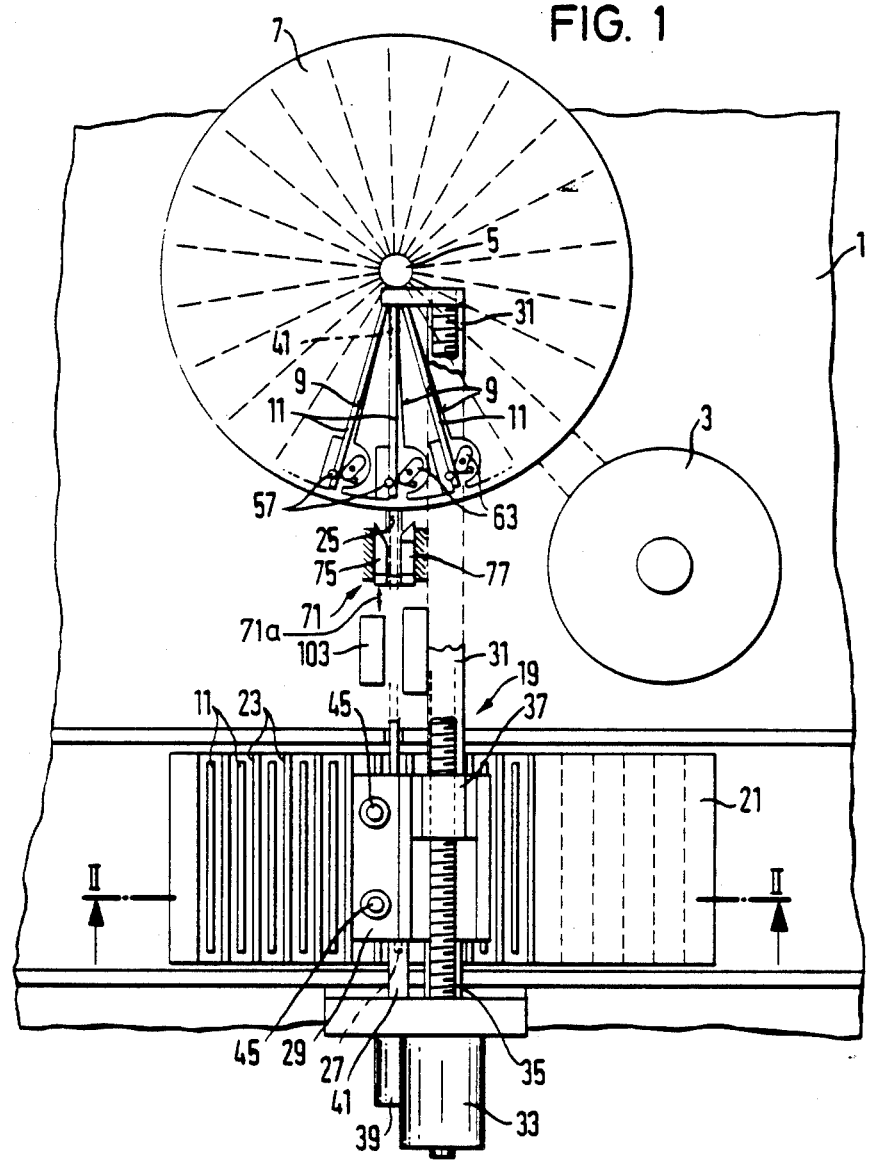
FIG. 1 is a schematic plan view of a centrifugal analysis apparatus.

The centrifugal analysis apparatus illustrated in FIG. 1, especially for the chemical analysis of blood and serum components, carries, on a schematically illustrated apparatus frame 1, a rotor 7 driven by an electric motor 3 around an axis of rotation 5. The rotor 7 has a plurality of guiding chambers 9 arranged with the same angular distances around the axis of rotation 5, which guiding chambers 9 run substantially radially and radially outwardly are open, into which can be inserted longitudinally extending insert elements 11, as is hereinafter explained in more detail. For ease of understanding, only three of the guiding chambers 9 are illustrated in FIG. 1.

As can best be seen from FIGS. 3 and 4, the insert elements 11 have, on their end facing the axis of rotation, an upwardly open supply opening 13 into which, in a manner which is not shown in detail, before the insertion of the insert elements 11 into the rotor 7, the liquid to be analysed is introduced in a predetermined amount. Each insert element 11 contains at least one mixing chamber in which the liquid to be analysed is, in the case of rotation of the rotor 7, mixed with a dry or liquid reagent already introduced into the insert element by the manufacturer. Furthermore, each insert element 11 includes, on its radially outer end, a cuvette or optical measurement chamber 15 in which the liquid to be analysed is introduced via communicating canals (not shown) from the mixing chamber or chambers upon rotation of the rotor 7. The rotation of the rotor 7 is, with regard to the speed of rotation and the period of time, so controlled that the mixing of the reagents, the incubation and the course of the reaction takes place in a predetermined manner. The path of rotation of the optical measurement chamber 15 crosses the beam path, indicated at 17 and running fixedly parallel to the axis of rotation of the rotor 7, of a photometer, which is not shown in detail, especially of a polychromic photometer operable at several wavelengths, which photometer measures the absorption of extinction of the liquid contained in the measurement chamber 15.

By means of a transport device schematically indicated by 19 in FIG. 1, the rotor 7 is supplied with insert elements which have also been provided automatically with the liquid to be analysed in a loading station, not shown in detail, placed before the analysis apparatus. For the transport of the insert elements, there are provided tray-shaped, flat magazines 21 which are movable by the transport device 19 substantially in the plane of the rotor 7 and tangentially to the rotor 7. The magazines 21 contain the insert elements 11 in trough-shaped recesses 23 which are open upwardly and in a side facing the rotor. The recesses 23 run parallel to one another and at right angles to the direction of movement of the magazine 21.

The transport device 19 selectively indexes each of the recesses 23 to a guiding canal schematically indicated by 25, which connects the recess present in an insert element exchange position aligned in a straight line with the guiding chamber 9 of the rotor 7 which is stationary for the exchange of the insert element. The guiding canal 25 is so constructed that the insert element to be pushed from the recess of the magazine 21 into the guiding chamber or removed from the guiding chamber into the recess of the magazine can be pushed or drawn during the whole of the movement path without having to be lifted up. For this purpose, the transport device 19 has a gripping means 27 which, in a manner described hereinafter in more detail, is held substantially vertically movably on a slider 29 of the transport device 19. The slider 29 is slidably removed on a slider guide 31 running parallel to the guiding chamber in an insert element-exchange or loading position at 25, i.e. substantially linearly between he magazine and rotor, and, when the gripping means 27 is lowered to grip an insert element releasably, transports insert elements from the recess 23 of the magazine into the guiding chamber 9 and vice versa.

In both directions of movement, the slider 29 is drivingly moved by a motor 33, flanged on to the apparatus frame 1, via a threaded spindle 35 parallel to the guide 31. The threaded spindle 35 cooperates with a non-sliding spindle nut 37. The stroke movement of the gripping means 27 is controlled by a motor 39, also flanged on to the apparatus frame 1, which motor 39 rotates a cam rod 41 about an axis of rotation parallel to the threaded spindle 35 and to the guide 31. The cam rod 41 extends over the whole movement path of the slider 29 and cooperates, as can best be seen from FIG. 2, with a holding means 43 of the gripping means 27. The holding means 43 is mounted vertically movably on two guide rods 45 on the slider 29 and is prestressed by screw pressure springs 47, which enclose the guide rods 45, upwardly against the cam rod 41. The cross-sectional profile of the cam rod 41 is so chosen that, in a first rotational position, the springs 47 can lift the gripping means 27 from the movement path of the insert elements 11 and, in a second position, the cam rod 41 drops down to the gripping means 27 in the movement path. The gripping means can be a fork which encloses the insert elements in the movement direction between its tines. However, on the insert elements there can also be provided openings extending in the stroke direction of the gripping means 27, into which openings there can engage, for example, pin-shaped gripping means.

Figure 2:
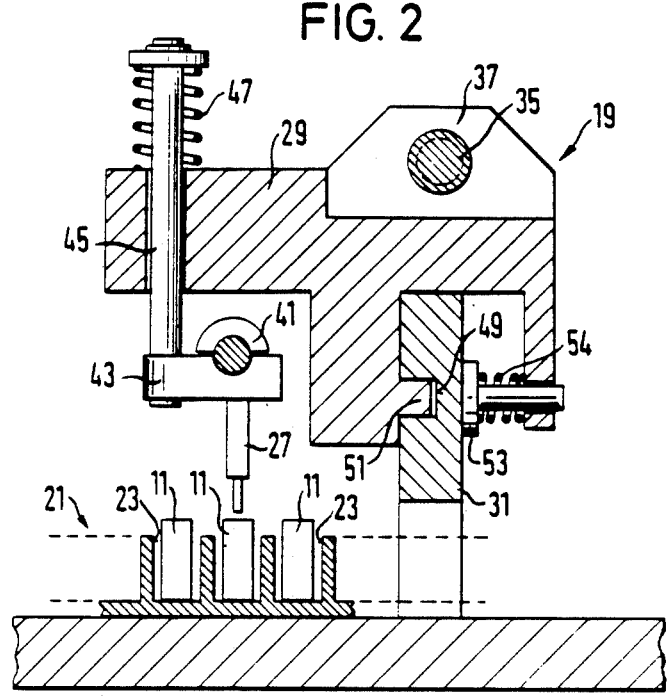
FIG. 2 is a schematic sectional view of a transport device for the supply of insert elements, seen along the line II—II of FIG. 1.

FIG. 2 shows details of the slider guide 31. The slider guide 31 is constructed as a flat-bed guide and has, on one of its flat sides, a groove 49 extending in the direction of movement, into which groove engages a rib 51 of the slider 29. A sliding plunger 53, movably mounted on the slider 29 transversely to the other flat side of the guide 31, is prestressed by a pressure spring 54, supported on the slider 29, against this other flat side.

The transport device 19 pushes the insert elements 11 substantially radially into the guide chamber 9, which is stationary in the insert element exchange position. In the circumferential direction of the rotor 7 laterally of the insertion path, there stands upwardly a positioning pin 57 in each guiding chamber 9 from a base plate 55 (FIG. 5) of the rotor 7. The guiding chamber 9 is so constructed that the insert element 11 can be pushed in the circumferential direction of the rotor 7 towards the positioning pin 57. The insert element carries a positioning trough 59 into which the positioning pin 57 engages when the insert element 11 is operationally inserted and the insert element 11 locates on the rotor 7, and also aligns to the beam path 17 of the photometer or its non-rotating trigger device. For increasing the positioning exactitude, the positioning trough 59 is provided closely adjacent to the measurement chamber 15 on the radially outer end of the insert element 11.

On the side of the insert element 11, remote from the positioning pin 57 in the circumferential direction, there is tiltably mounted, on a peg 61 parallel to the axis of rotation, a double-armed lever 63, as can best be seen from FIG. 3. The lever 63 has two arms 65 and 67 projecting substantially diametrically to the peg 61, of which the arm 65 is placed, in the radial direction of the rotor, on the outer side of the peg 61 and the arm 67 is placed on the inner side. A leaf spring 69 fixed on to the rotor prestresses the lever 63 by its arm 67 via a ledge 67a thereon with such a direction of tilt that the arm 65 is tilted towards the positioning pin 57. The leaf spring 69 pushes the insert element 11, pushed radially into the guiding chamber 9 by the transport device 19, in the circumferential direction of the rotor 7 towards the positioning pin 57 and holds the positioning pin 57 in engagement with the positioning trough 59. The arm 67 runs in this engagement position to the side of the peg 61 remote from the positioning pin 57. Its weight and its shape are such that its moment of rotation caused by the centrifugal acceleration is greater than that of the arm 65 so that it acts as a flyweight which strengthens the stopping force of the leaf spring 69 in the case of rotation of the rotor 7.

An insert element 11 to be withdrawn by the transport device 19 from the guiding chamber 9 is released by an ejector fork 71 from the location of the positioning pin 57. The ejector fork 71 is movable, as FIG. 1 shows schematically with arrow 71a, radially to the rotor 7 at the guiding canal 25. In FIGS. 3 and 4, the direction of movement is indicated by double arrows 73. In the resting position, the ejector fork 71 is present outside of the rotary path of the rotor 7. It is taken up by the slider 29 of the transport device 19 and pushed into the rotary path of the rotor 7. The ejector fork 71 has, on opposite-lying sides of the guiding canal 25, an ejector or disengaging finger 75 and a locking finger 77. The ejector finger 75, projecting in the insert element exchange position on the side of the positioning pin 57 towards the rotor 7, carries on its free end an oblique surface 79 projectingly including away from the positioning pin 57 relative to the guiding cannal 25, which oblique surface 79 pushes the positioning trough 59 of the insert element located on the positioning pin 57 in the circumferential direction of the rotor 7 out of engagement with the fixed element positiioning pin 57. Surfaces of the locking finger or movable lock 77, as guide surfaces, locate a guiding chamber 9 in the insert element exchange position, by moving into a locking canal 81 on the side of the peg 61 remote from the insert element 11 in the circumferential direction of the rotor 7. This locks the rotor and its guiding chamber 9 fixedly there. The locking finger 77 is so dimensioned that the rotor 7 is located before the oblique surface 79 begins to eject the insert element 11.

On its free end, the locking finger 77 carries frontfacedly a pushing surface 83 which cooperates with an associated pushing surface 85 of the lever arm 67 and, with the rotor 7 locked, lifts up the lever arm 65, against the resistance of the leaf spring 69, from the insert element 11. Furthermore, on the locking finger 77, there is provided a stop surface 87 pointing counter to its insertion direction. On the lever arm 65, there is provided a stop lug 89 with a stop surface 91 directed counter to the stop surface 87. The stop lug 89 and the stop surface 87 are so arranged that the stop surface 91 of the stop lug 89 is outside of the movement path of the locking finger 77 when the insert element 11 is correctly positioned on the positioning pin 57.

If the lever 63 is tilted by the pushing surface 83, then the stop lug 89 engages behind the stop surface 87. The stop lug 89 prevents the drawing back of the ejection fork 71 when the insert element 11 is incorrectly located, for example when the positioning pin 57, because of radial misalignment, cannot engage into the positioning trough 59. Control circuits, which are not illustrated in detail and are operated by the ejection fork 71, prevent the setting into operation of the motor 3 and thus the throwing out of the non-located insert element 11.

FIG. 3 shows the ejection fork 71 with unbroken lines in its stationary position, i.e. in the case of the rotor 7 being free to rotate. FIG. 3 shows with broken lines the ejection fork 71 in a position in which the rotor 7 is already locked by the locking finger 77 but the ejection fork 71 is, however, still not pushed sufficiently into the rotor that the ejection finger 75 has freed the insert element 11 from its anchoring. FIG. 4 shows the ejection fork 71 in the position in which the ejection finger 75 has lifted the insert element 11 from the positioning pin 57 and the locking finger 77 has lifted the lever arm 65 from the insert element 11.

In FIG. 5, 93 and 95 indicate parts of the optics or of the photodetector or light sources of the photometer, the beam path 17 of which passes through axial borings, not shown in detail, of the base plate 55. The indexing of the base plate 55 is controlled by a one-piece control pin 97 formed on the positioning pin 57. The control pin 97 projects on the side of the base plate 55 axially remote to the guiding chamber 9 and crosses the beam path of a control light barrier indicated by 99, which triggers a source of flash light or the like of the photometer when the measurement chamber 15 of the insert element 11 crosses the beam path 17. Since the control pin 97 is formed in one piece with the positioning pin 57, the trigger exactitude is increased.

The positioning exactitude of the measurement chamber 15 relative to the positioning pin 57 can be further increased when insert elements made as synthetic resin formed parts are used in which the positioning trough 59 and the cylinder wall of the essentially semi-cylindrical measurement chamber are formed from shaping surfaces of the said one-piece shaping tool part, for example in an injection moulding process.

Figure 6:
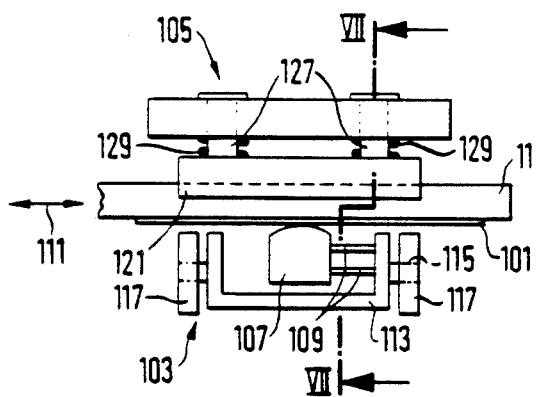
FIG. 6 is a plan view of a magnet head reading device of the analysis apparatus according to FIG. 1.

The operation of the centrifugal analysis apparatus is controlled according to a predetermined programme, dependent upon data which are stored on a magnetic layer 101 (FIG. 6) on a surface of the insert element 11 which is lateral in the direction of movement. The magnetic layer 101 can carry additional data which serve for the identification of the sample. Result data can possibly be stored on the magnetic layer 101. The data are read off or recorded by means of a magnetic head unit 103 during the displacement movement of the insert element 11. A guiding unit 105 guides the insert element 11 while it is being passed by the magnetic head unit 103. In FIG. 1, the magnetic head unit 103 is positioned in the region of the guiding canal 25 between the magazine 21 and the rotor 7. However, the magnetic head unit 103 can also be in another position, especially in the region of a device supplying the insert elements of the magazine with liquid samples.

Figure 7:
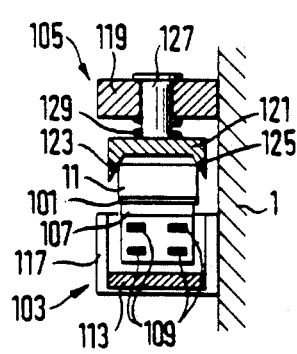
FIG. 7 is a schematic sectional view of the reader device, seen along the line VII—VII of FIG. 6.

The magnetic head unit 103 and the guiding unit 105 are so constructed that the magnetic layer 101 lies against the whole length of the working slot of a magnet head 107 (FIGS. 6 and 7) of the magnetic head unit 103. The magnet head 107 is held on four springs 109 on a frame 113. It is flexibly deflectable transversely to the direction of movement of the insert element 11, indicated by an arrow 111. The frame part 113 is mounted on flanges 117 fixed to the apparatus frame and is tiltable about an axis of rotation 115 running in the direction of movement 111. The guiding unit 105 carries on a flange 119, fixed to the apparatus frame, a guiding rail 121 with two guiding surfaces 123, 125 inclined towards one another in the direction away from the magnet head 107. The guiding surfaces 123, 125 inclined towards one another guide the opposite-lying longitudinal edges of the side surface remote from the magnetic layer 101. Because of this guiding, the insert element 11 can tilt about its longitudinal axis. The guiding rail 121 is movably mounted on the flange 119 on two pegs 127 transversely to the direction of movement 111 and is prestressed by pressure springs 129 towards the magnet head unit 103.

Figure 8:
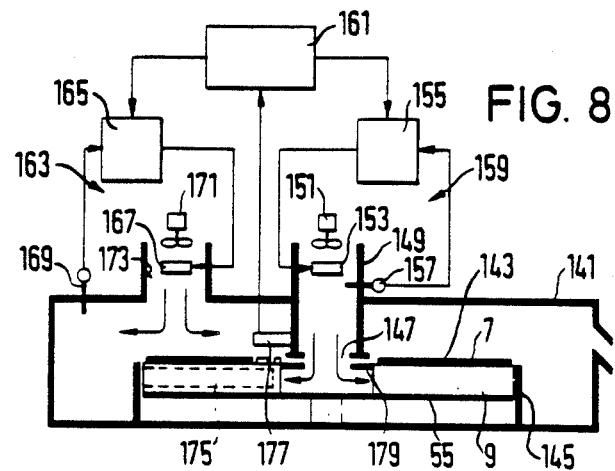
FIG. 8 is a schematic illustration of the temperature regulating devices for maintaining constant the rotor temperature.

FIG. 8 shows, in a block diagram, details of the temperature regulating devices for keeping constant the temperature of the rotor 7. The rotor 7 is arranged in a housing 141, the inner chamber of which, essentially formed by the guiding chambers 9 and receiving the insert elements, is almost completely closed towards the interior of the housing. The lower side of the inner chamber is formed by the already mentioned base plate 55, the upper side being formed by a covering plate 143 or by a a plurality of lids which upwardly close of the guiding chambers 9 and are deflectable by a the gripping means of the previously mentioned transport device. The peripheral surface of the rotor 7 is closed by a wall 145 fixed to the housing, which wall surrounds the peripheral surface at a small distance therefrom and essentially only leaves open the insertion opening of the insert element exchange position.

Into a central opening 147 on the upper side of the rotor 7, there opens an air canal 149 which supplies warm air from a source of warm air produced by a ventilator 151 and a heating element 153, which warm air tempers the inner chamber of the rotor 7. The heating element 153 and/or possibly the ventilator 151 form, together with a regulator 155 and a temperature sensor 157 measuring the air temperature, for example in the canal 149, a temperature-regulating circuit 159 which maintains the temperature of the air supplied to the inner chamber of the rotor 7 at a desired value, predeterminable by means of a control 161.

A second temperature-regulating circuit 163 regulates the temperature of the air in the interior of the housing 141 but outside of the rotor 7. The regulating circuit 163 includes a regulator 165, which maintains a heating element 167 at a desired value predetermined by the control 161, dependent upon the air temperature measured by means of a temperature sensor 169 in the interior of the housing 141. In FIG. 8, the heating device 167 is provided in the region of an air inlet opening 173 provided with a ventilator 171. Embodiments are also preferred in which the heating device overlaps a large surface area of the rotor.

The desired values of the regulating circuits 159, 163 can be adjusted independently of one another. The regulators 155, 165 are preferably PID regulators, i.e. regulators with proportional, integral and differential behaviour. With the help of such regulating circuits, the internal temperature of the rotor 7 can be kept constant within very small limits of error, even during the rotational operation, for example at 37±0.1° C. In order to monitor the actual inner temperature as accurately as practically possible, in one of the guiding chambers there is provided a temperature sensor indicated by 175 in FIG. 8. The temperature sensor sits in a housing, the dimensions and shape of which correspond to the shape of the insert elements. An opto-coupler indicated by 177 transmits the temperature information to the control 161. The energy supply of the temperature sensor 175 takes place via slip rings 179 or in an inductive-transformatory way. The temperature information of the temperature sensor 175 can be utilised for the control of the desired value of at least one of the two temperature control circuits. In order to take into account the temperature change in the interior of the rotor 7 in the case of the centrifugal operation, the control 161 can be so constructed that it changes the desired value of the regulating circuit 159 a predetermined period of time before commencement of the centrifugal operation by a predetermined correction amount, for example lowers in the case of a comparatively high surrounding temperature in order to counteract a subsequent warming up due to surrounding air sucked in by the centrifuging.

Figure 9:
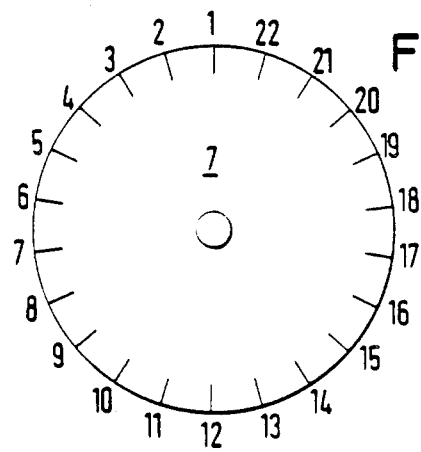
FIG. 9 is a schematic illustration of the rotor of the analysis apparatus according to FIG. 1 for the explanation of the imbalance compensation carried out by a control according to a predetermined loading and/or unloading programme.

Imbalance oscillations of the rotor have a disadvantageous effect on the measurement exactitude of the centrifugal analysis apparatus. The imbalance oscillations can be reduced to a minimum when the loading and unloading of the rotor is so controlled by a control means that, after insertion or removal of a predetermined number of insert elements determining the maximum imbalance, in each case the same number of insert elements is inserted or removed from the essentially diametrically opposite-lying side of the rotor. FIG. 9 shows the rotor schematically, the holding means or guiding chambers being numbered counterclockwise from 1 to 22. If only the imbalance brought about by a single insert element is permitted, then the rotor can be loaded, for example, according to the following scheme: 1-12-2-13-3-14 etc. If the imbalance of two insert elements is permitted, then the loading scheme could be 1,2-12,13-3,4-14,15 etc. The unloading of the rotor can take place according to an analogous scheme.

In the case of the above loading or unloading scheme, after the loading or unloading of a predetermined number of insert elements, the rotor is, in each case, rotated through about 180°. The loading or unloading time can be shortened when, after the loading or unloading of the predetermined number of adjacent holding means of the rotor, in the same supply rotational direction, alternatingly either the predetermined number of adjacent holding means lying substantially diametrically opposite to the last-loaded holding means are loaded or unloaded or the predetermined number of holding means adjacent the last-loaded holding means are loaded or unloaded in the supply rotational direction. In the case of a maximum imbalance of a single insert element, the loading or unloading scheme could be as follows: 1-12-13-2-3-14-15 etc. In the case of a maximum imbalance of two insert elements, the loading or unloading scheme is 1,2-12,13-14,15-3,4-5,6 etc.

Insofar as, as has been explained with reference to FIG. 8, one of the holding means of guiding chambers is always occupied by a temperature sensor element, the imbalance of this element must, of course, be taken into account. The loading cycle commences, therefore, on the holding means lying diametrically opposite to the temperature element, the loading cycle being counted from the temperature sensor element.

Figure 10:
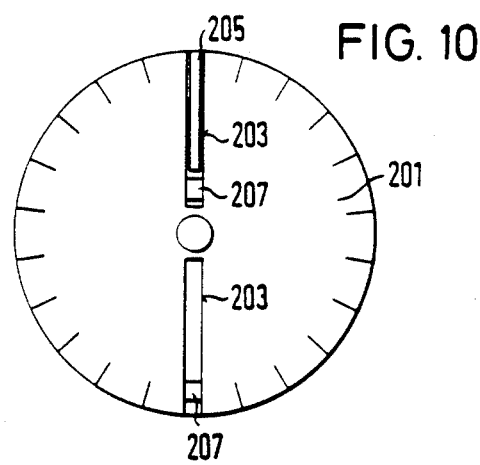
FIG. 10 is a schematic illustration of a rotor which can be used in the analysis apparatus according to FIG. 1, with flyweights for the imbalance compensation in the case of a rotor partly loaded with insert elements.

FIG. 10 shows schematically a rotor 201 which can be used instead of the rotor 7, which rotor 201 has a flyweight 207 for each holding means 203 of an insert element 205. The flyweight 207 is movable between a radially outer position shown at the bottom of FIG. 10 and a radially inner position shown at the top of FIG. 10, for example by the use of an insert element 205. In the radially inner position, the flyweight 207 is located by the inserted insert element 205. The inner position, the outer position, the weight of the flyweight 207 and weight of the insert element 205 are such that the centrifugal force produced by the flyweight 207 present in the outer position in the case of absence of an insert element is the same as the centrifugal force which is produced by the insert element and the flyweight present in the inner position. In the case of such a rotor, the holding means can be loaded or unloaded randomly.

Figure 11:
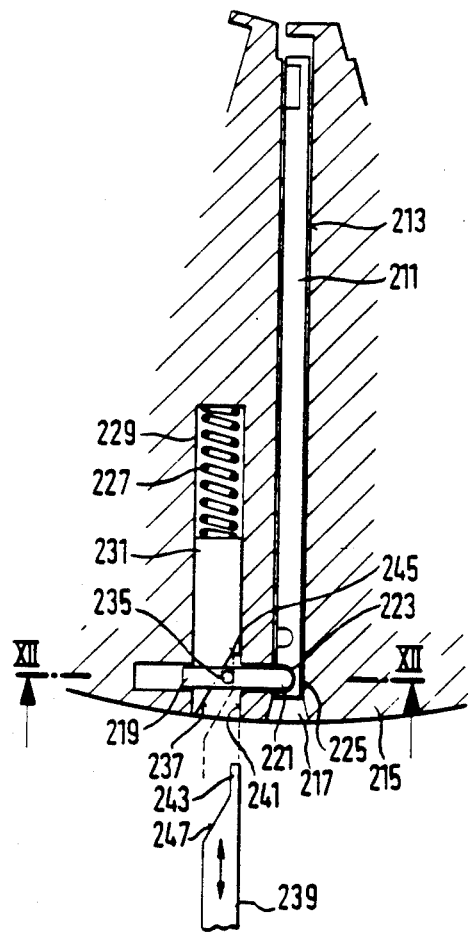
FIG. 11 is a schematic partial section of another embodiment of a rotor which can be used in the centrifugal analysis apparatus according to FIG. 1, with inserted and positioned insert element.
Figure 12:
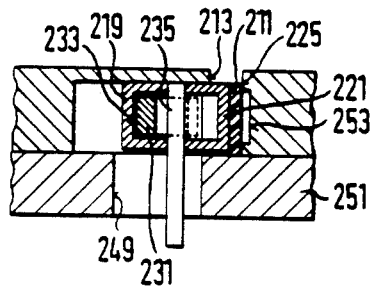
FIG. 12 is a sectional view of the rotor along the line XII—XII of FIG. 11.

FIGS. 11 and 12 show another embodiment of a holding means for an insert element 211, corresponding to the insert element 11 of FIG. 1. The insert element 211 sits in a substantially radially running guiding canal 213 of a rotor 215 rotatable around a central axis of rotation. The rotor 215 has a plurality of such guiding chambers 213 which are distributed around its axis of rotation with the same angular distances. The insert elements 211 have a longitudinally extended shape and rectangular cross-section. A transport device, not illustrated in detail, similar to the transport device 19 in FIG. 1, introduces the insert element 211 automatically via an opening 217 into the guiding chamber 213.

Laterally of the insert path of each guiding chamber 213 is movably mounted on the rotor 215 a positioning element 219 tangentially to the radial direction of the guiding chamber 213. The positioning element 219 carries on its end facing the direction of movement of the guiding chamber 213, a positioning ledge 221 which, in the sliding position remote from the guiding chamber 213, frees the insertion cross-section of the guiding chamber 213 and, in the other sliding position, engages in a positioning trough 223 of the insert element 211, which trough 223 is open towards the positioning element 219. The insert element 211 inserted into the guiding chamber 213 is pressed by the positioning element 219 against a side wall 225 pointing in the circumferential direction of the rotor 215 and positions in the circumferential direction. In the radial direction, the insert element 211 is positioned and locked by the positioning ledge 221 engaging in the positioning trough 223. The positioning element 219 is shown in FIG. 12 as a frame; however, it can also have another shape, for example it can be U-shaped.

For producing the pressing-on force of the positioning element 219, there is provided a pressure spring 227 which, in a chamber 229 of the rotor 215, prestresses a pressure piece 231 substantially radially outwardly towards the positioning element 219. The radially outer end of the pressure piece 231 passes through an opening 233 of the positioning element 219 in which runs a pin 235 fixed on to the positioning element 219, parallel to the axis of rotation of the rotor 215. The part of the pressure piece 231 engaging in the opening 233 has a wedge shape and has a pushing surface 237 inclined to the direction of movement of the pressure piece 231 and also parallel to the axis of rotation of the rotor 215. The pushing surface 237 engaging on the pin 235 presses the positioning element, by the action of the pressure spring 227, towards the side surface 225 of the guiding chamber 213. The angle of incidence of the pushing surface 237 to the direction of movement of the pressure piece 231 is, for increasing the pressing-on force, preferably selected to be smaller than 45°.

For the unlocking of the insert element 211, on the apparatus frame, which is not shown in detail, there is mounted an operating finger 239, which is slidable in the direction of movement of the pressure piece 231. The operating finger 239, which, in the rotational operation of the rotor 215, is present outside of its path of rotation, engages, when the rotor 215 is stationary in an insert element exchange position, through a locking opening 241 into the rotor 215 and locates this non-rotatably. The end of the operating finger 239 facing the pressure piece 231 carries a lug 243 which passes through the opening 233 of the positioning element 219 and can impinge against a counter-directed shoulder 245 of the pressure piece 231. In the course of the pushing-in movement of the operating finger 239, the lug 243 lifts the pushing surface 237 of the pressure piece 231 from the pin 235 of the positioning element 219. Following the lug 243, the operating finger 239 has a pushing surface 247 directed counter to the pushing surface 237. The pushing surface 247 runs parallel to the pin 235 and obliquely to the direction of movement of the operating finger 239 and of the positioning element 219. The lug 243 is so dimensioned that the operating finger 239 lifts the pressure piece 231 from the pin 235 and thus frees from the pressure force of the spring 227 before the pushing surface 247 impinges against the pin 235 and the positioning element 219 moves out of the insertion path of the guiding chamber 213. In this way, the guiding surfaces of the positioning element 219 and its guidings on the rotor side are protected even when the spring forces exerted on the positioning element 219 are so large that they can overcome slight deformations of the insert element 211 which hold it at a distance from the side wall 225.

The pin 235 projects through a slot 249 in a base plate 251 of the rotor and, corresponding to the control pin 97 in FIG. 5, is utilised for the control of a control light barrier, not shown in detail, which triggers the source of flashlight of the photometer.

The guiding chamber 213 guides the insert element essentially only in the region of its edges. At least in the side surfaces of the guiding chambers 213, facing the circumferential direction, there are provided air-conducting canals 253, only one of which is shown in FIG. 12. As is described in more detail with reference to FIG. 8, the air-conducting canals 253 are connected with a temperature-regulating source of air. Since the temperature-regulating air is conducted in close contact along the side surfaces of the insert elements, there is provided an especially short time constant for the temperature regulation.

When an insert element 211 is inserted into the guiding chamber 213, the pressure pieces 231 are present in a radially inwardly-lying position, whereas when the guiding chamber 213 is empty, they occupy a radially outwardly-lying position. By appropriate dimensioning of the weight of the pressure element 231, an imbalance equalisation can be achieved, as is described in more detail with reference to FIG. 10.

Figure 13:
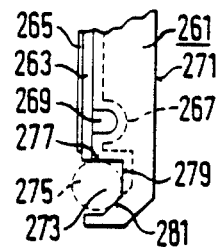
FIG. 13 is a partial view of the end, carrying a positioning means, of an insert element which can be used in the rotors of FIGS. 1 and 11, seen in the radial direction of the rotor.

FIG. 13 is a partial plan view of an insert element, seen in the axial direction of the rotor. It includes a longitudinally extending base body 261, made as a synthetic resin formed part, for example by an injection moulding process, in which, from one of its side surfaces, there are formed, in a manner not shown in detail, all the canals and chambers necessary for the measurement reactions. The canals and chambers are closed by a tightly fixed strip-shaped plate 263, for example by an ultrasonic welding process. The plate 263 has a flat surface and is provided with a magnetic data carrying layer 265, as explained in more detail with reference to FIGS. 6 and 7. The side surface lying opposite the plate 265, as is indicated by a broken line at 267 for an optical measurement chamber 269, follows the shape of the chambers and canals. On the narrow side surfaces, lying opposite the plate 263, are formed side walls 271 which, along the longitudinal edges of the insert element, form guiding surfaces which guide the insert element into the guiding chamber.

The insert element carries, referred to its rotor position, radially outside of the optical measurement chamber 269, a positioning trough 273 running parallel-axially to the axis of rotation of the rotor, into which trough 273 can engage the positioning means of the rotor-side holding means, indicated by 275 and also axially parallel. The positioning trough 273 opens in the direction of the side of the insert element, thus transversely to the longitudinal extension of the insert element. It is formed substantially semicircularly. The positioning trough 273 and the trough of the optical measurement chamber 269 closely adjacent thereto and formed in the base part 261 are so shaped that they are formed by a one-piece moulding tool which does not have to be opened for removal from the mould. In this way, the production tolerances of the positioning trough 273 relative to the optical measurement chamber 269 can be reduced.

The positioning trough 273 has a bearing surface 277 running at right angles to the longitudinal direction of the insert element, which surface 277 determines the radial position of the insert element relative to the optical beam path of the photometer, and a surface 279 running in the longitudinal direction, which fixes the position in the circumferential direction of the rotor. A surface 281 running obliquely to the bearing surface 277 but parallel to the axis of rotation of the rotor, helps to bring the bearing surface 277 close to the positioning means 275, the bearing surface 277 thereby lying against it completely during the centrifugal operation. In the embodiment according to FIG. 1, the bearing surface 279 is pressed by means of the lever 63 against the rotor-fixed pin 57. In the embodiment according to FIG. 11, a surface corresponding to the bearing surface 279 is formed by the guiding surfaces of the side walls 271, which lie against the side wall 225. However, the positioning trough 273 can also, seen from the direction of the rotor axis, have a rectangular cross-section.

The bearing surfaces of the positioning trough can also be so constructed in another manner that they ensure a reproducible and exact positioning of the insert element. It is thereby important that the bearing surfaces and the rotor-fixed positioning means 275, preferably formed as a pin, do not come into contact over a large surface, such as would be the case if the positioning trough 273 were formed exactly semicircularly with a radius adapted to the pin 275. In this case, even slight tolerance changes in the formation of the positioning tough 273 could have the result that the positioning trough 273 either jams on the pin 275 or has too much play and thus exact and especially reproducible positioning would not be possible. In contradistinction thereto, in the case of a construction in which the positioning trough 273 lies with only two or three narrow, almost linear-shaped surfaces on the pin 275, there is always ensured a reproducible positioning, even in the case of unavoidable tolerances in the production of the positioning trough.

It will be understood that the specification and examples are illustrative but not limitative of the present invention and that other embodiments within the spirit and scope of the invention will suggest themselves to those skilled in the art.

What is claimed is:

1. A photometric liquid analysis apparatus of the centrifugal analysis type, comprising:
   at least one insert element comprising an elongated body, an optical measurement chamber near one end of the elongated body and a positioning trough on one side of the elongated body;
   a rotor for rotating the at least one insert element to photometric means for photometric analysis of a liquid in the optical measurement chamber of the at least one insert element, during rotation of the rotor, with a beam of the photometric means which cuts the path of rotation of the optical measurement chamber of the at least one insert element on the rotor;
   at least one guiding chamber, each guiding chamber positioned in the rotor along a radius thereof and having an opening at an end thereof adjacent the outer periphery of the rotor, each guiding chamber configured to receive an insert element for its rotation by the rotor with the positioning trough on the side of the insert element being on a lateral side thereof and adjacent the outer periphery of the rotor as received in its respective guiding chamber; and
   positioning and holding means on the rotor for positioning the optical measurement chamber of each insert element in its respective guiding chamber at a position adjacent the outer periphery of said rotor and holding the insert element therein during the rotation of the rotor, the positioning and holding means comprising a fixed element in a fixed position relative to the rotor on a lateral side of each guiding chamber at a position adjacent the outer periphery of the rotor and facing the positioning trough of the insert element circumferentially spaced therefrom when the insert element is initially received in its respective guiding chamber in a first position therein, and adjustment means for moving the received insert element circumferentially into a second position engaging the fixed element with the positioning trough thereof;
   whereby said positioning trough and said fixed element are in a locking configuration in said second position.

2. Analysis apparatus according to claim 1, wherein the fixed element comprises a pin projecting from the rotor perpendicular to the plane of the rotor.

3. Analysis apparatus according to claim 2, wherein the rotor has a base disc having an axial bore therethrough and the pin sits in the axial bore of the base disc of the rotor and passes therethrough to a side of the base disc axially away from the positioning and holding means for forming a control pin for a control light.

4. Analysis apparatus according to claim 1, wherein the adjustment means comprises a level tiltably mounted on the rotor and a spring positioned and arranged so that a first end of the spring forcibly impinges against the rotor and a second end of the spring forcibly impinges against the level, whereby said spring causes said level to forcibly impinge against the received insert element.

5. Analysis apparatus according to claim 4, wherein the first end impinges against a lateral wall of the guiding chamber and the adjustment means further comprises a ledge protruding from the lever and positioned and arranged so that the second end of the spring impinges against the ledge, whereby said lever is caused to impinge against the received insert element thereby moving the received insert element into said second position engaging said fixed element with the positioning trough of said received insert element.

6. Analysis apparatus according to claim 1, and further comprising a movable lock in the apparatus, the movable lock having guide surfaces positioned and arranged to locate and lock a guiding chamber of the rotor located at an insert element-exchange position of the apparatus at the insert element-exchange position of the apparatus when the movable lock is moved to a first position.

7. Analysis apparatus according to claim 6, wherein the movable lock further comprises disengaging means to bring the positioning and holding means out of engagement with the positioning trough of an insert element received in a guiding chamber located at the insert element exchange positioning when the movable lock is moved into the first position.

8. Analysis apparatus according to claim 6, wherein the adjustment means is a lever tiltably mounted on the rotor and means effective upon rotation of the rotor for forcibly impinging the lever against the insert element received in the guiding chamber in the direction of the fixed element.

9. Analysis apparatus according to claim 8, wherein the lever is tiltably mounted about an axis parallel to the axis of rotation of the rotor on the side of the guiding chamber lying opposite to the fixed element in the circumferential direction of the rotor.

10. Analysis apparatus according to claim 9, wherein the movable lock is movably mounted substantially radially to the rotor and, on a free end of the movable lock facing the rotor, carries a pushing surface which is positioned and arranged to engage a pushing surface on an arm of the lever on a side of the lever facing away from the received insert element when the movable lock is positioned in the first position.

11. Analysis apparatus according to claim 6, wherein the at least one guiding chamber comprises a plurality of guiding chambers and wherein the analysis apparatus further comprises at least one magazine which has a plurality of recesses for insert elements, the magazine having an opening therein in a side thereof facing said rotor, means for selectively indexing each one of the plurality of recesses to a position adjacent said opening, transport means for removing an insert element from a recess located adjacent the opening and transporting an insert element so removed to an insert element loading position adjacent said rotor and for returning an insert element at the loading station to a recess in the magazine located adjacent the opening and means for inserting an insert element from the loading position into a guiding chamber located adjacent the loading position.

12. Analysis apparatus according to claim 11, wherein the transport means comprises a slider guide running substantially linearly between the magazine and the rotor, a slider movable along the slider guide, a controllable drive connected to the slider for moving the slider along the slider guide between the loading position and a position in the region of the magazine, and gripping means on the slider for releasably gripping an insert element.

13. Analysis apparatus according to claim 12, wherein the transport means comprises a cam rod rotatably mounted on the apparatus for rotation about an axis parallel to the slider guide, and means for sliding the slider along the cam rod to displace the slider and, in a first rotational position, bringing the gripping means into engagement with an insert element located in a recess adjacent said opening in said magazine and, in a second rotational position, out of engagement therewith.

* * * * *

UNITED STATES PATENT AND TRADEMARK OFFICE
CERTIFICATE OF CORRECTION

PATENT NO. : 4,676,952

DATED : June 30, 1987

INVENTOR(S) : Hermann Edelmann, et al.

It is certified that error appears in the above-identified patent and that said Letters Patent is hereby corrected as shown below:

Column 7, line 1: change "holding means" to -- guiding chambers --.

Column 8, line 68: after "23 to" insert -- a position adjacent --.

Column 8, line 68: change "canal" to -- channel in an insert element exchange position as --.

Column 9, line 1: change "by" to -- at --.

Column 10, line 48: change "cannal" to -- canal --.

Column 18, lines 8 and 9: change "level" to -- lever --.

Column 18, line 34: change "positioning" to -- position --.

Signed and Sealed this

Seventeenth Day of May, 1988

Attest:

DONALD J. QUIGG

Attesting Officer

Commissioner of Patents and Trademarks